(12) United States Patent
Overmyer

(10) Patent No.: US 10,052,164 B2
(45) Date of Patent: Aug. 21, 2018

(54) SYSTEM AND METHOD OF CONVERTING USER INPUT INTO MOTION OF A SURGICAL INSTRUMENT VIA A ROBOTIC SURGICAL SYSTEM

(71) Applicant: Ethicon Endo-Surgery, LLC, Guaynabo, PR (US)

(72) Inventor: Mark D. Overmyer, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 127 days.

(21) Appl. No.: 15/282,353

(22) Filed: Sep. 30, 2016

(65) Prior Publication Data

US 2017/0095295 A1 Apr. 6, 2017

Related U.S. Application Data

(60) Provisional application No. 62/236,356, filed on Oct. 2, 2015.

(51) Int. Cl.
*A61B 34/30* (2016.01)
*A61B 34/00* (2016.01)
(Continued)

(52) U.S. Cl.
CPC ........ *A61B 34/30* (2016.02); *A61B 17/07207* (2013.01); *A61B 17/320092* (2013.01);
(Continued)

(58) Field of Classification Search
CPC ......... A61B 34/30; A61B 34/74; A61B 34/25; A61B 34/20; A61B 17/07207; A61B 18/1445; A61B 17/320092; A61B 2017/00212; A61B 17/320068; A61B 2090/372; A61B 2034/2055;
(Continued)

(56) References Cited

U.S. PATENT DOCUMENTS 6,783,524 B2 8/2004 Anderson et al.
8,768,516 B2 * 7/2014 Diolaiti ................. B25J 9/1689
700/262

(Continued)

OTHER PUBLICATIONS

U.S. Appl. No. 15/282,243, filed Sep. 30, 2016.
U.S. Appl. No. 62/236,356, filed Sep. 30, 2016.

*Primary Examiner* — Jaimie Figueroa
(74) *Attorney, Agent, or Firm* — Frost Brown Todd LLC

(57) ABSTRACT

A wireless handheld user input device may be moved within six degrees of freedom in order to generate position data that describes the position and angular orientation of the user input device within three-dimensional space. Position data is received by a position management device and is interpreted to reduce the input data from six degrees of freedom down to a number of degrees of freedom that is supported by a surgical instrument adapted to be manipulated by a robotic surgical system. Position data is interpreted by taking raw overlap data showing the change from a baseline position to a current position and correcting it to zero out inputs for unsupported degrees of freedom that do not exceed a device or device portion specific threshold. The converted overlap data may then be used to generate new joint target positions, which may be communicated to the robotic surgical system.

20 Claims, 10 Drawing Sheets

(51) Int. Cl.
*A61B 34/20* (2016.01)
*B25J 13/08* (2006.01)
*B25J 13/02* (2006.01)
*A61B 18/14* (2006.01)
*A61B 17/00* (2006.01)
*B25J 13/00* (2006.01)
*A61B 17/072* (2006.01)
*A61B 17/32* (2006.01)
*A61B 90/00* (2016.01)

(52) U.S. Cl.
CPC .......... *A61B 18/1445* (2013.01); *A61B 34/20* (2016.02); *A61B 34/25* (2016.02); *A61B 34/74* (2016.02); *B25J 13/006* (2013.01); *B25J 13/02* (2013.01); *B25J 13/088* (2013.01); *B25J 13/089* (2013.01); *A61B 17/320068* (2013.01); *A61B 2017/00212* (2013.01); *A61B 2034/2048* (2016.02); *A61B 2034/2051* (2016.02); *A61B 2034/2055* (2016.02); *A61B 2090/372* (2016.02)

(58) Field of Classification Search
CPC ..... A61B 2034/2051; A61B 2034/2048; B25J 13/089; B25J 13/088; B25J 13/02; B25J 13/006

USPC .................................................. 700/245, 253
See application file for complete search history.

(56) References Cited

U.S. PATENT DOCUMENTS

| | | | |
|---|---|---|---|
| 8,989,528 B2* | 3/2015 | Udd | A61B 5/06 385/10 |
| 9,084,623 B2* | 7/2015 | Gomez | A61B 19/2203 |
| 2003/0182091 A1* | 9/2003 | Kukuk | G05B 17/02 703/2 |
| 2010/0332033 A1* | 12/2010 | Diolaiti | B25J 9/1689 700/259 |
| 2011/0040305 A1* | 2/2011 | Gomez | A61B 19/2203 606/130 |
| 2014/0039681 A1* | 2/2014 | Bowling | A61B 34/32 700/261 |
| 2014/0222207 A1* | 8/2014 | Bowling | A61B 34/32 700/261 |
| 2015/0374446 A1* | 12/2015 | Malackowski | A61B 19/2203 606/130 |

\* cited by examiner

SYSTEM AND METHOD OF CONVERTING USER INPUT INTO MOTION OF A SURGICAL INSTRUMENT VIA A ROBOTIC SURGICAL SYSTEM

PRIORITY

This application claims priority to U.S. Provisional Patent App. No. 62/236,356, entitled "User Input Device (UID) and Guided User Interface (GM) for a Robotic Surgical System," filed October 2, 2015, the disclosure of which is incorporated by reference herein.

BACKGROUND

Robotic controls may be used in a wide variety of surgical procedures. For example, in minimally invasive robotic surgery, surgical operations may be performed through a small incision in the patient's body. In addition to a wide variety of surgical procedures, a robotic surgical system may be used with various types of surgical instruments, including but not limited to surgical staplers, ultrasonic instruments, electrosurgical instruments, suturing instruments, and/or various other kinds of instruments.

A robotic surgical system may include an operation assembly and a control assembly, which may be positioned in separate locations. An operation assembly may include various cameras and robotic arms configured to operate on a patient. Cameras may be used to capture desired images of a patient and robotic arms during a procedure. Robotic arms may connect to and manipulate various compatible surgical equipment in order to physically perform a surgical procedure. A control assembly may include a viewing screen and various user input devices. The viewing screen may be used to view images provided by the cameras of the operation assembly. The user input devices may be used in order to manipulate the robotic arms and the compatible surgical equipment attached to the robotic arms. In other words, an operator may remotely perform a surgical procedure with the user input devices of the control assembly and the robotic arms of the operation assembly, while simultaneously viewing the surgical procedure with the cameras of the operation assembly and the viewing screen of the control assembly.

In some robotic surgical systems, the user input devices are physically attached to the rest of the control assembly. Therefore, while the robotic arms may connect to and manipulate various compatible surgical equipment, the same user input devices must be used in order to control various surgical equipment attached to the robotic arms.

Some conventional robotic instruments may be mechanically capable of orienting the end effector of a particular instrument within a three-dimensional space with six degrees of freedom, commonly referred to as up and down, left and right, forward and back, yaw, pitch, and roll. With a robotic tool arm, a user input device may also support movement and corresponding user input with six degrees of freedom. Thus, a user of a robotic tool system input device may move the input device within three-dimensional space, including rotational movements, and those movements may be captured as input and provided to a robotic tool arm to produce corresponding movements of the tool.

However, not all tools or surgical end effectors are capable of movements or manipulation for all six degrees of freedom. For example, one robotic tool may have a cutting or clamping end effector that articulates about one axis on a joint between the end-effector and the distal portion of a shaft that supports the end-effector. In such a situation, user input received from an input device may include inputs for movement for six degrees of freedom, which may force the robotic system to interpret such inputs into five degrees of freedom or less when determining what corresponding movements the tool or end effector should make. If the robotic system misinterprets the intention of the user when converting from six degrees of freedom to five degrees of freedom or less, the robotic tool arm may be moved in a manner that is unintended by the user of the user input device. This could result in the robotic arm either ignoring a movement that a user intended entirely, or performing a movement that the user did not intend, both of which would be undesirable in many robotic tool arm settings.

While a variety of systems have been made and used for managing and converting user inputs for a robotic tool arm, it is believed that no one prior to the inventor(s) has made or used the technology as described herein.

BRIEF DESCRIPTION OF THE DRAWINGS

It is believed the present invention will be better understood from the following description of certain examples taken in conjunction with the accompanying drawings, in which like reference numerals identify the same elements and in which.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims, For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Robotic Surgical System

Figure 1:
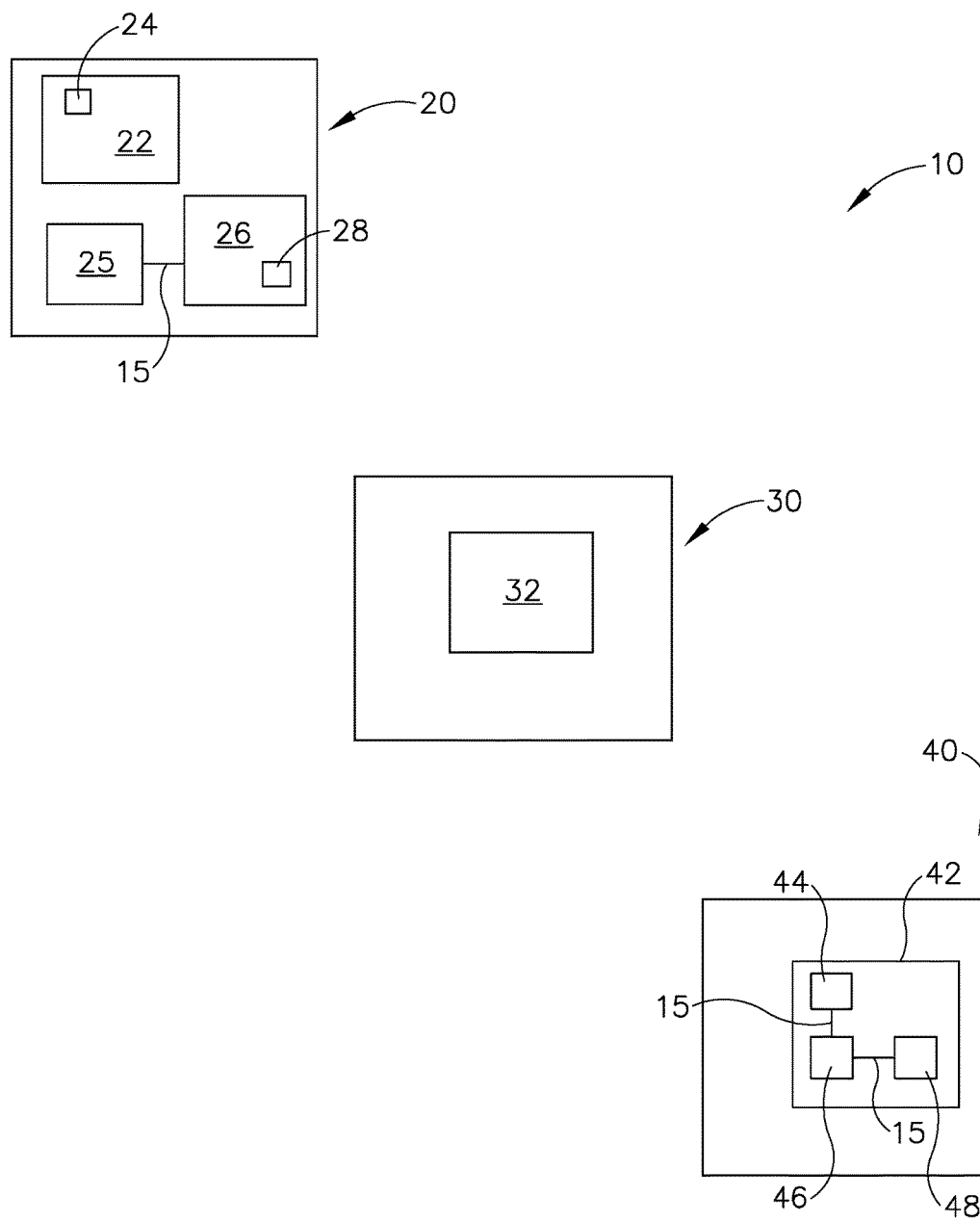
FIG. 1 depicts a schematic diagram of an exemplary robotic surgical system.

FIG. 1 shows a schematic diagram of an exemplary robotic surgical system (10). Robotic surgical system (10) includes an exemplary control assembly (20), an exemplary data transmission unit (30), and an exemplary operation assembly (40). As will be described in greater detail below, control assembly (20) is configured generate commands that are used to actuate operation assembly (40) to perform a desired surgical procedure.

Operation assembly (40) includes a robotic surgical assembly (42) that is configured to operate on a patient. Robotic surgical assembly (42) includes a communication device (44), a processing device (46), and a robotic actuation assembly (48). Robotic actuation assembly (48) may include one or multiple movable robotic arms that are attached to various surgical instruments, such as surgical staplers, ultrasonic surgical instruments, electrosurgical instruments, suturing instruments, endoscopic cameras, sensors, and/or various other kinds of instruments that would be apparent to one having ordinary skill in the art in view of the teachings herein. Additionally, robotic arms may actuate, articulate, control, and/or activate corresponding attached surgical instruments in any suitable manner that would be apparent to one having ordinary skill in the art in view of the teachings herein. As will be described in greater detail below, control assembly (20) may control functions of robotic actuation assembly (48), such as movement of robotic arms and control of attached surgical instruments.

In the present example, robotic actuation assembly (48) is in communication with processing device (46) via communication wire (15), though this communication may be provided wirelessly if desired. Processing device (46) is operable to instruct robotic actuation assembly (48) on precise movements and actions of the robotic arms and surgical instruments that are attached to the robotic arms. Additionally, sensors, endoscopic cameras, and other suitable instrumentation of robotic actuation assembly (48) may provide feedback information to processing device (46).

Processing device (46) is also in communication with communication device (44) via communication wire (15), though again this communication may be wireless in some versions. Communication device (44) establishes communication between data transmission unit (30) and processing device (46). Processing device (46) is operable to receive instructions from transmission unit (30) via communication device (44). Processing device (46) may further interpret those instructions and transmit them to robotic actuation assembly (48). Therefore, robotic actuation assembly (48) may move robotic arms and move, articulate, control, and/or activate attached surgical instruments in response to transmitted instructions from data transmission unit (30) to robotic actuation assembly (48) via communication device (44). Communication device (44) may also transfer data from processing device (46) to data transmission unit (30), such as data from sensors or endoscopic cameras within robotic actuation assembly (48).

Data transmission unit (30) includes a server (32), which may receive, store, and transmit information to and from operation assembly (40), as described above, and exemplary control assembly (20), as will be described in greater detail below. In other words, server (32) may act as an intermediary between control assembly (20) and operation assembly (40). In some versions, server (32) may also store at least some of the communications between control assembly (20) and operation assembly (40). Server (32) may utilize any suitable means of receiving, storing, and transmitting information as would be apparent to one having ordinary skill in the art in view of the teachings herein. It should be understood that storing information on server (32) is merely optional. Therefore, server (32) may strictly act as an intermediary between control assembly (20) and operation assembly (40). It should also be understood that control assembly (20) and operation assembly (40) may be coupled with server (32) using any known networking components and techniques. Moreover, in some versions, control assembly (20) and operation assembly (40) are in direct communication with each other, such that data transmission unit (30) may simply be omitted.

Control assembly (20) includes a user input device assembly (22) containing a first wireless communication device (24), a processing device (26) containing a second wireless communication device (28), and an exemplary viewing screen (2) in communication with processing device (26) via a communication wire (15) (though again this coupling may be wireless if desired). As will be described in greater detail below, user input device assembly (22) may instruct robotic actuation assembly (48) to move and/or activate as described above.

User input device assembly (22) is physically separated from processing device (26). Therefore, user input device assembly (22) may be freely moved relative to the rest of control assembly (20), provided that a communication link is maintained between wireless communication devices (24, 28). User input device assembly (22) is configured to be grasped by an operator in order to generate control signals, which are sent to first wireless communication device (24). First wireless communication device (24) is in communication with second wireless communication device (28) such that control signals may be sent from user input device assembly (22) to second wireless communication device (8). Additionally, second wireless communication device (28) may also send information to first wireless communication device (28).

Second wireless communication device (28) may selectively establish communication with first wireless communication device (24). By way of example only, wireless communication devices (24, 28) may communicate with each other using Bluetooth or any other suitable protocol or modality. Registration of user input device assembly with processing device (26) may be achieved through a digital handshake or any other suitable method that would be apparent to one having ordinary skill in the art in view of the teachings herein. Therefore, multiple or different user input device assemblies (22) may be utilized with the rest of control assembly (20). In other words, user input device assemblies (22) may be switched out for alternative user input device assemblies (22) depending on the preference of an operator. It should also be understood that various kinds of user input device assemblies (22) may be used by a single operator within a single surgical procedure. In such scenarios, the various user input device assemblies (22) may simultaneously maintain registration with processing device (26); or user input device assemblies (22) may be serially registered and de-registered with processing device (26), such that only one user input device assemblies (22) is registered with processing device (26) at a given moment during a surgical procedure. Other suitable registration and communication scenarios will be apparent to those of ordinary skill in the art in view of the teachings herein.

Second wireless communication device (28) is also in communication with both processing device (26) and data transmission unit (30). Therefore, second wireless communication device (28) may send control signals received from first wireless communication device (24) to both processing device (26) and server (32) of data transmission unit (30). As mentioned above, data transmission unit (30) is also in communication with processing device (46) of robotic assembly (42) via communication device (44). Processing device (46) may control movement of robotic actuation assembly (48). Therefore, control signals generated by user input device assembly (22) may control robotic actuation assembly (48) via wireless communication devices (24, 28), first processing device (26), server (32), communication device (44), and second processing device (46).

Second wireless communication device (28) may also receive information from data transmission unit (30). As mentioned above, data transmission unit (30) may receive data from sensors, endoscopic cameras, other suitable instrumentation of robotic actuation assembly, or any other information generated by operation assembly (40). Therefore, second wireless communication device (28) may send processing unit (26) information from operation assembly (40), which may be interpreted and processed by processing device (26) and displayed on viewing screen (25) and/or user input device assembly (22).

While in the current example, user input device assembly is in wireless communication with processing device (26), any other suitable communication means may be used as would be apparent to one having ordinary skill in the art in view of the teachings herein. For example, a communication wire (15) may connect processing device (26) and user input device assembly (22).

In exemplary use, an operator may be located at control assembly (20) while a patient is located at operation assembly (40). The operator may view live images generated by endoscopic cameras of robotic actuation assembly (48) on viewing screen (5) and/or other cameras within operation assembly (40). While viewing live images generated by endoscopic cameras of robotic actuation assembly (48), the operator may grasp and manipulate user input device assembly (22) and thereby generate desired control signals, which in turn instruct surgical instruments of robotic actuation assembly (48) to operate on the patient.

It should be understood that control assembly (20), data transmission unit (30), and operation assembly (40) may all be located at different locations. Alternatively, any suitable combination of control assembly (20), data transmission unit (30), and operation assembly may be located at the same location as would be apparent to one having ordinary skill in the art in view of the teachings herein. For example, control assembly (20) and data transmission unit (30) may be located in a first building, while operation assembly (40) may be located at a second building miles away. Additionally, data transmission unit (30) may be incorporated into portions of control assembly (20) and/or operation assembly (40).

It should also be understood that since control assembly (20) may be located at a difference location than an operator, an operator may manipulate operation assembly (40) while stationed at a different location. For instance, in some scenarios, the operator and the patient are hundreds or thousands of miles apart from each other during the surgical procedure. In some other scenarios, the operator and the patient are on the same campus or in the same building but are in separate rooms from each other. In still other scenarios, the operator and the patient are in the same room as each other. Other suitable scenarios relating to operator-patient positioning will be apparent to those of ordinary skill in the art in view of the teachings herein.

II. Robotic Surgical System User Input Mapping

In order to improve the responsiveness and safety of robotic surgical system (10) it may be desirable to configure one or more of the devices of FIG. 1 to interpret user inputs that are generated by the input device assembly (22) and passed to actuate operation assembly (40) in a manner that minimizes unintended movements of the surgical instruments of the robotic actuation assembly (48). This may be particularly desirable in situations where, for example, an input device assembly (22) is generating input data in six degrees of freedom ("6DoF") while operation assembly (40) or robotic actuation assembly (48) can only translate input data into corresponding movements of a surgical instrument in five degrees of freedom or less (e.g. "5DoF," "4DoF," etc.). For example, while the input device assembly (2) may be freely moved or rotated in any direction, a particular surgical instrument or surgical instrument end effector may be restricted to 3DoF movement within three-dimensional space and may be unable to rotate about any axis.

One implementation of the technology described herein may store a baseline position and orientation of an input device assembly (22) as well as device angles for shaft, yaw, and pitch at the moment that the input device assembly (22) receives a signal indicating that a user intends subsequent movements to correspondingly affect a surgical instrument, which may be referred to as "clutching." It should be understood that "clutching" may occur when the user actuates a clutching feature of input device assembly (22) or some other clutching feature (e.g., footswitch) that is operable to generate a clutching signal in response to user input, to demonstrate the user's intent to manipulate the robotic arm and/or surgical instrument attached to the robotic arm of robotic actuation assembly (48). Merely illustrative examples of ways in which an input device assembly (22) and/or other components of a robotic surgical system (10) may provide clutching are described in U.S. Pub. No. 2017/0095298, entitled "User Input Device for Robotic Surgical System," published Apr. 6, 2017, the disclosure of which is incorporated by reference herein. Similarly, various suitable forms that input device assembly (22) may take are disclosed in U.S. Pub. No. 2017/0095298, published Apr. 6, 2017.

At the moment of clutching, an equivalent input device assembly (22) position and orientation may be calculated by comparing the current position and orientation to a stored "input axis" position and orientation, thereby generating a baseline. The instrument axes angle targets (800 and/or 802 and/or 804) are updated by the portion of an input angle corresponding to the amount of overlap between input axes vector and the vector corresponding to the axes of the instrument degrees of freedom.

Some implementations may calculate this overlap by finding the dot product between the input axis and each instrument axis, and applying a deadband so that, if the absolute value of the overlap does not exceed a predefined value or threshold, the updated angle target for any axis with overlap outside the deadband is zero. If the overlap does exceed the threshold, the value may be changed monotonically at the threshold values. In this manner, movements of the input device assembly (22) intended to move a subset of device angles, but which may actually result in slight changes to angles outside of the subset, will prevent unintentional movements in surgical instruments corresponding to those slight changes that fall outside of the subset of intended changes. With this method, device angles can be limited by the physical constraints of the surgical instrument that is receiving inputs from the input device assembly (22). For example, if the surgical instrument or end effector is limited to movement on a single plane, rotational movements such as pitch, yaw, or shift can be limited to zero. Various exemplary features, implementations, and details of such a method are described below.

In a 6DoF system, coordinates can be described by their x, y and z positions with respect to the global world frame, and their orientation matrix. The orientation matrix is composed of unit vectors (i-hat, j-hat and k-hat) aligned with the x, y and z axes of the local coordinate system, as reflected on the x, y and z axes of the global world frame.

Examples of orientation matrices can be found in tables 1, 2 and 3 below.

TABLE 1

An exemplary orientation matrix showing unit vectors of a selected origin.

| i-hat$_1$ | j-hat$_1$ | k-hat$_1$ |
| i-hat$_2$ | j-hat$_2$ | k-hat$_2$ |
| i-hat$_3$ | j-hat$_3$ | k-hat$_3$ |

TABLE 2

An exemplary orientation matrix showing unit vectors of the local coordinate system that align with the global coordinate system.

| 1 | 0 | 0 |
| 0 | 1 | 0 |
| 0 | 0 | 1 |

TABLE 3

An exemplary orientation matrix showing the local x unit vector aligning with the global y axis, the local y unit vector aligning with but pointing in the opposite direction of the x axis of the global coordinate system, and the local z unit vector aligning with the global z axis.

| 0 | −1 | 0 |
| 1 | 0 | 0 |
| 0 | 0 | 1 |

Figure 2:
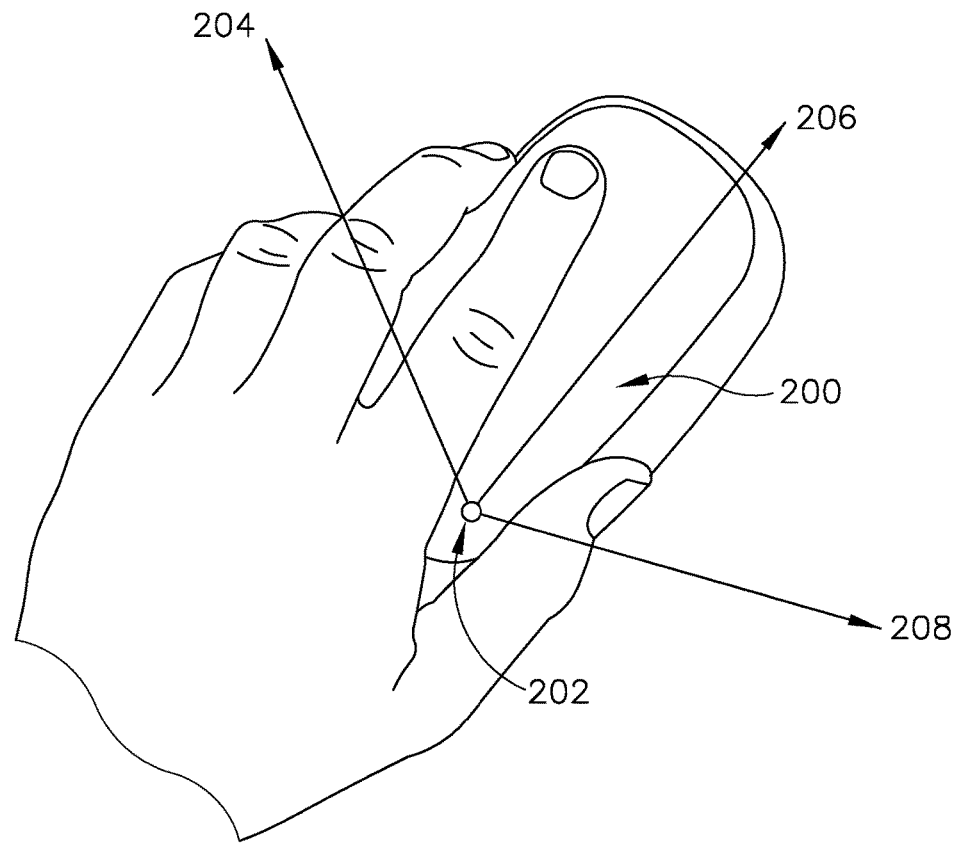
FIG. 2 depicts an exemplary handheld user input device that may be used with the robotic surgical system of FIG. 1.

FIG. 2 shows one example of an input device assembly (22) that may be grasped in the hand and manipulated with 6DoF. FIG. 2 further shows how such a device relates to the unit vectors of an orientation matrix system. The user input device (200) has an origin point (202) at which its orientation is measured from with respect to its position within the z plane and k-hat unit vector (204), the y plane and j-hat unit vector (206), and the x plane and j-hat unit vector (208).

Figure 3:
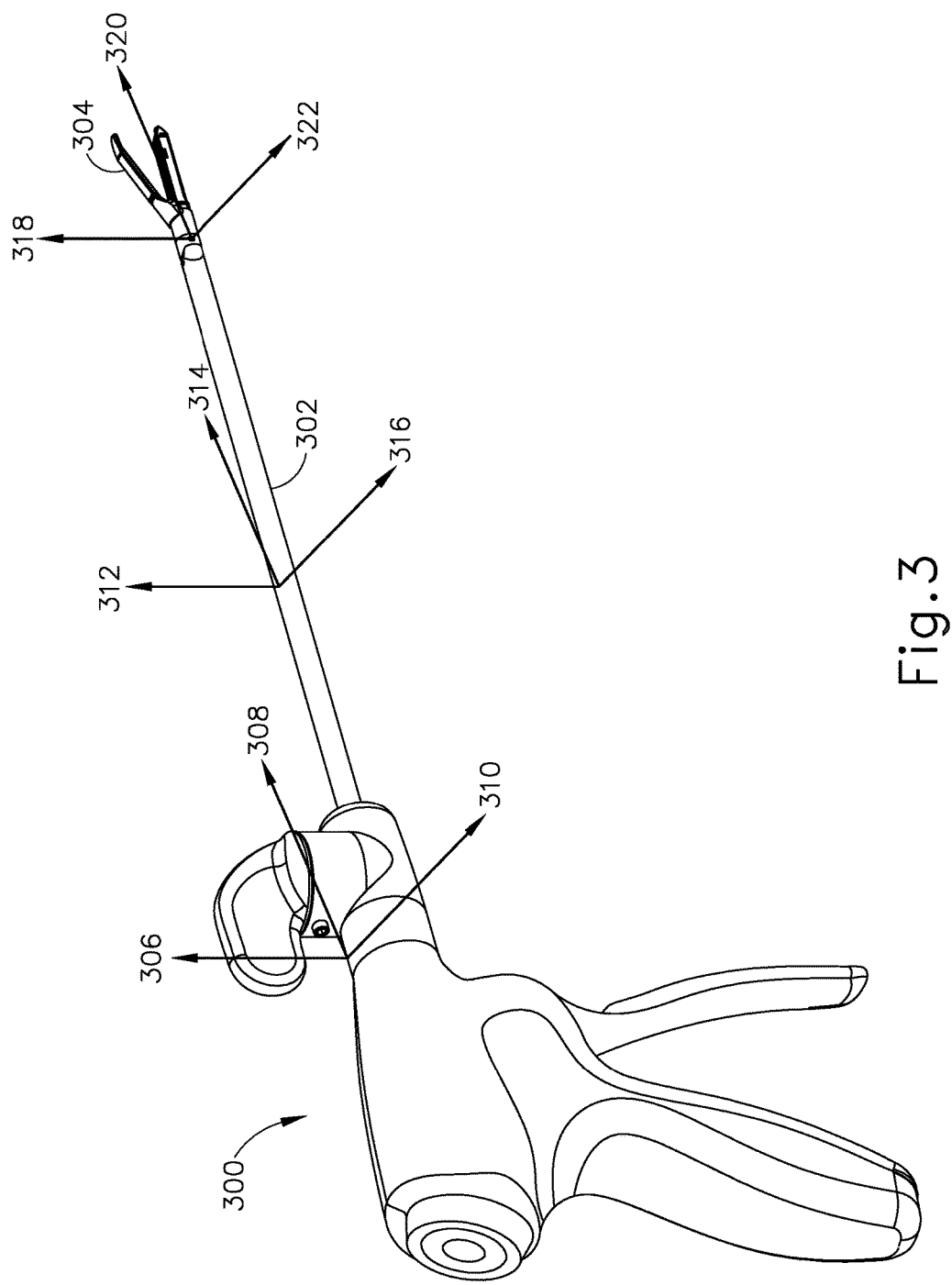
FIG. 3 depicts an exemplary surgical instrument with separately movable and rotatable portions.
Figure 4:
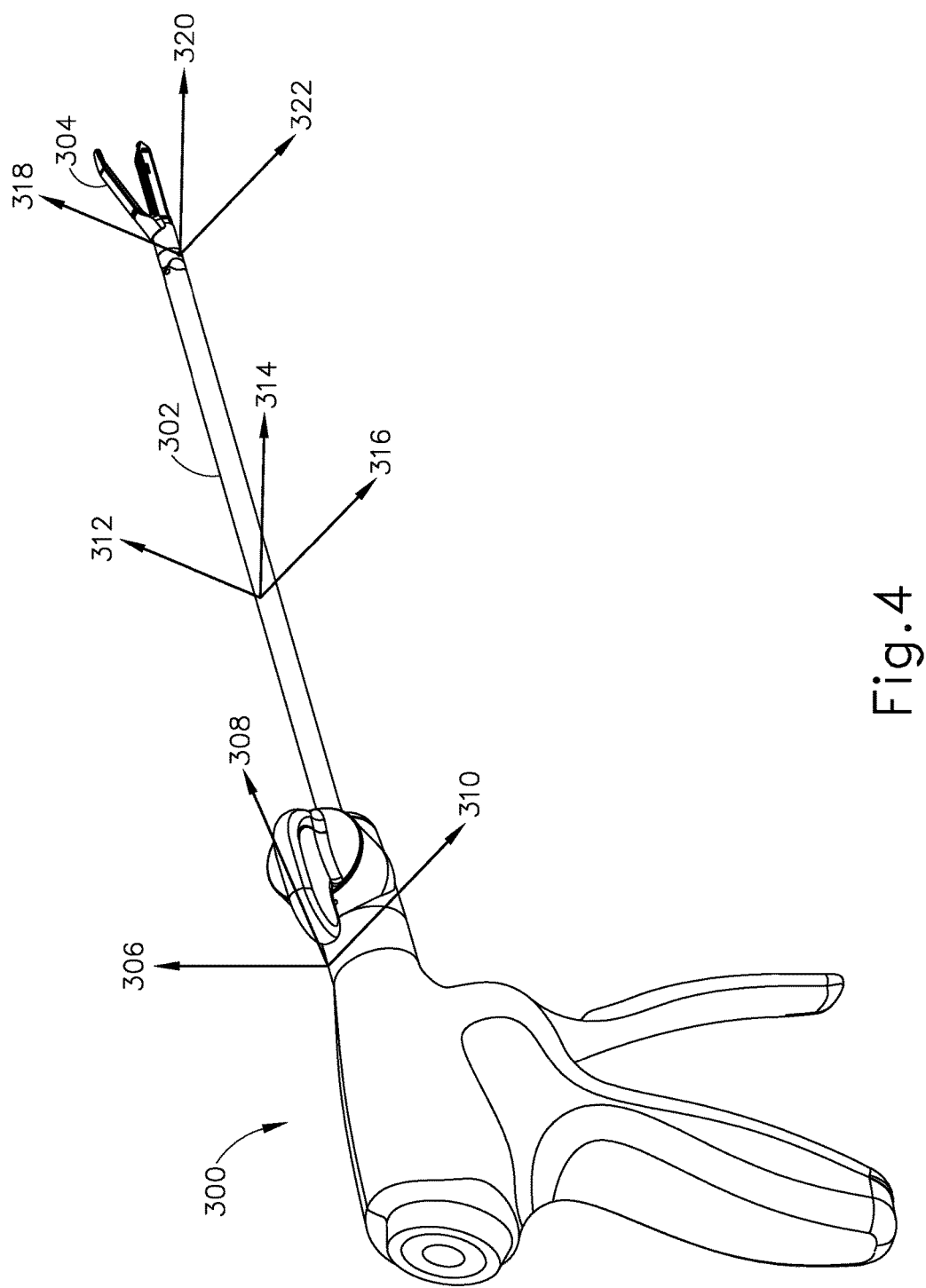
FIG. 4 depicts the surgical instrument of FIG. 3 after rotation of a shaft assembly of the surgical instrument.
Figure 5:
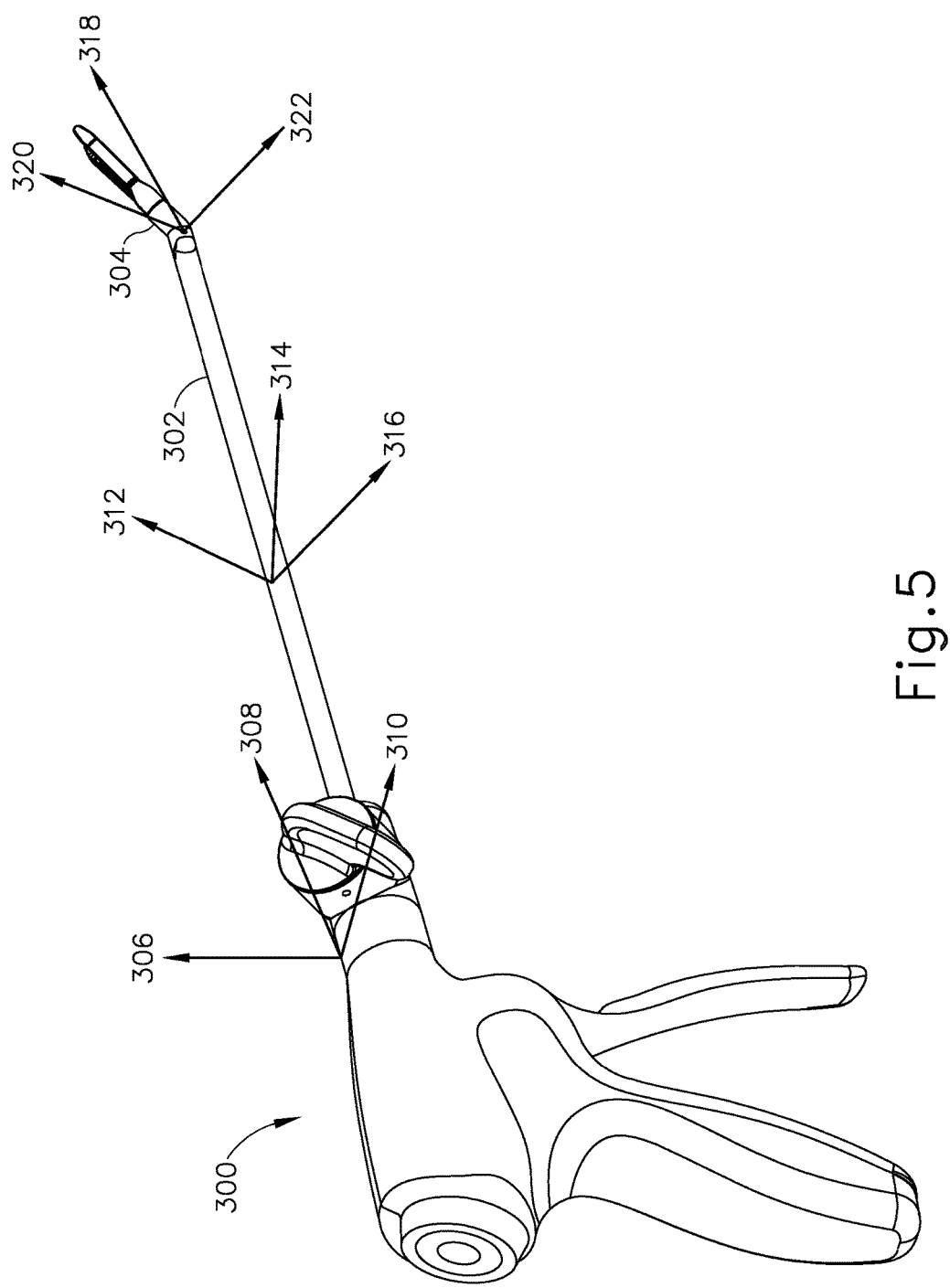
FIG. 5 depicts the surgical instrument of FIG. 4 after articulation of an end of the surgical instrument.
Figure 6:
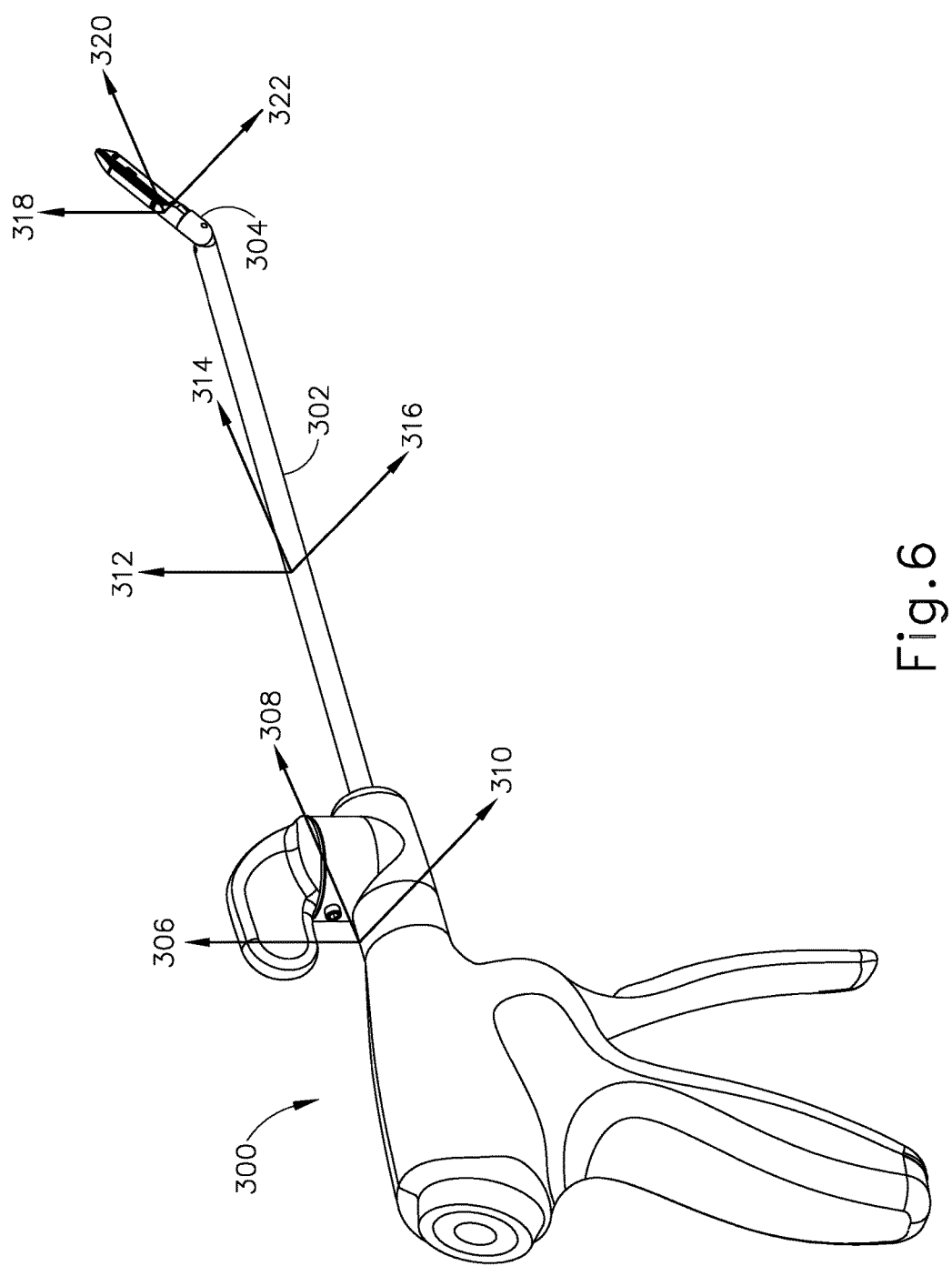
FIG. 6 depicts the surgical instrument of FIG. 5 after rotation of the shaft assembly back to the original position of FIG. 3.

It should also b o d that a series of local coordinate systems may be associated with a single surgical instrument, or with separate features or components of a single surgical instrument, FIGS. 3-6 show examples of such an implementation. Referring to FIG. 3, coordinate system "0" (i.e., $x_0$, $y_0$, and $z_0$) may be set with its y-axis (308) extending along the shaft (302) of a surgical instrument (300), its z-axis (306) in the plane made up of the shaft and the z-axis of the global coordinate system, and the x-axis (310) orthogonal to the z and y axes such that the tight-hand rule is followed. Coordinate system "1" (i.e., $x_1$, $y_1$, and $z_1$) may be set with its y-axis (314) parallel to $y_0$ (308), but with its x-axis (316) and z-axis (312) able to be rotated about $y_1$ by shaft rotation, as shown in FIGS. 4 and 5, Coordinate system "2" (i.e. $x_2$, $y_2$, and $z_2$) may have its z-axis (318) parallel to $z_1$, but its x-axis (322) and y-axis (320) are able to be rotated about z2 by yaw rotation, as shown in FIGS. 5 and 6.

In the implementation shown in FIGS. 3-6, shaft rotation and yaw rotation are examples of joint angle targets. There could also be a pitch angle associated with a fourth reference axis to allow the end effector (304) to move along an additional degree of freedom, if a surgical instrument (300) supported such movement. Joint angle targets can be assigned to axes of the coordinate systems, and the coordinate systems may rotate about the assigned axis in the magnitude of the joint angle. With several points of rotation, the rotations may build on each other such that a rotation of a proximal coordinate system about an axis according to a joint angle will cause a distal coordinate system to move through an arc (i.e., in an orbital movement about the same axis about which the proximal coordinate system rotates).

Figure 10:
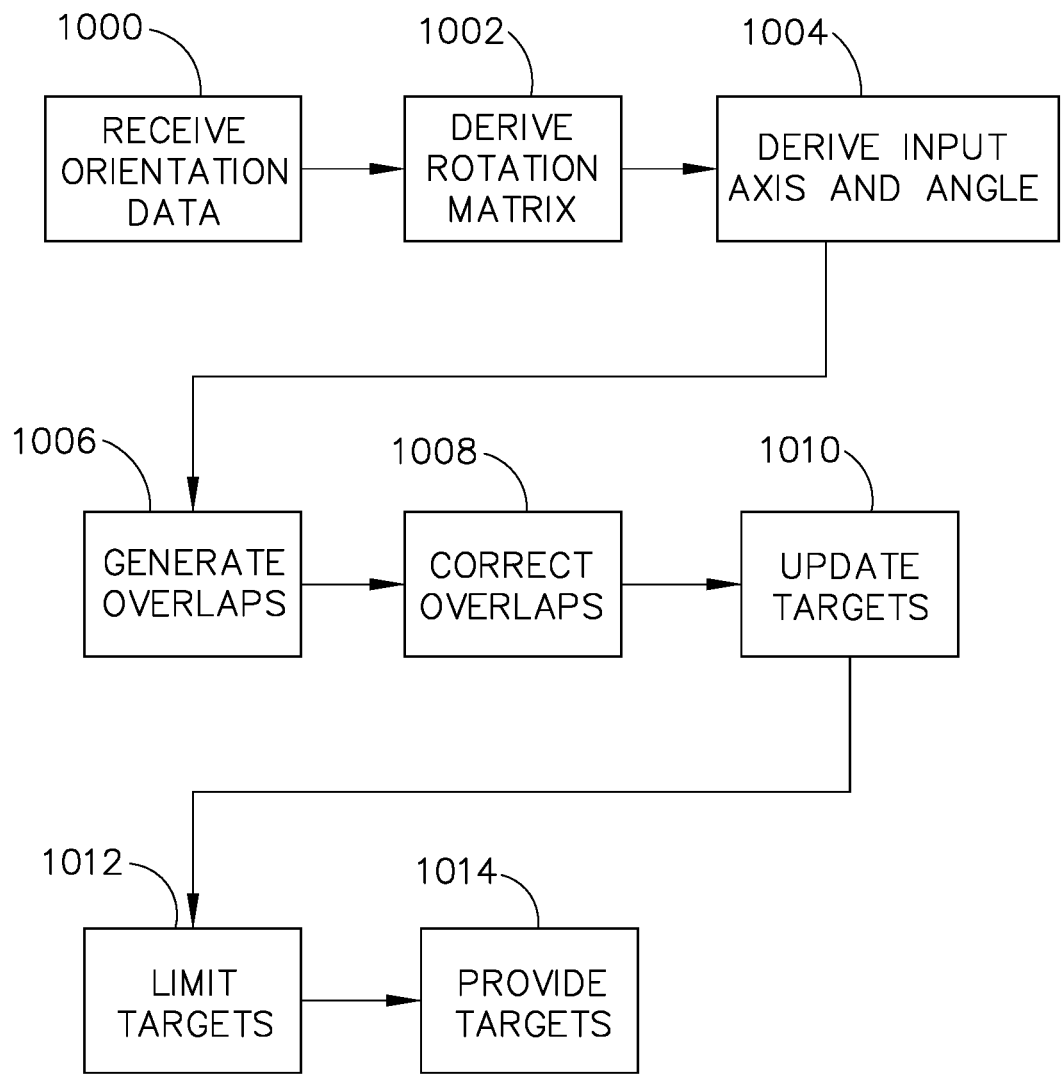
FIG. 10 depicts an exemplary set of steps that may be performed by the robotic surgical system of FIG. 1 to interpret a set of position data with six degrees of freedom for use with a surgical instrument supporting less than six degrees of freedom.

FIG. 10 shows an exemplary set of steps that may be performed by a version of robotic surgical system (10) that is configured to interpret movement and rotation of a user input device (200) to a corresponding movement or rotation of a surgical instrument (300) when the input device (200) generates inputs with 6DoF and the surgical instrument (300) is only capable of movements and rotations within 5DoF or less. In some versions, the steps shown in FIG. 10 are performed by processing device (26). In some other versions, the steps shown in FIG. 10 are performed by server (32). In still other versions, the steps shown in FIG. 10 are performed by processing device (46). Other suitable components that may be used to perform the steps shown in FIG. 10 will be apparent to those of ordinary skill in the art in view of the teachings herein.

The steps of FIG. 10 allow orientation matrices generated by a user input device (200) to drive the position, or one or more positions, of a surgical instrument (300). In this manner, robotic surgical system (10) may interpret the relative orientation of the user input device (200) to command the joint angle targets used to configure the surgical instrument (300) coordinate systems described above in FIGS. 3-6. At a high level, joint angle targets may be updated according to the amount of overlap between the equivalent axis of rotation of the user input device (200) and the axis associated with the joint angle target along with the magnitude of rotation of the user input device (200). The overlap is then corrected to include a threshold and scale factor such that the motion of the user input device (200) can adapt or "snap" to the axes that highly overlap and ignore axes that only partially overlap, resulting in a decrease of unintentional movements of the surgical instrument (300).

Initially, robotic surgical system (10) may receive (block 1000) initial orientation data in the form of a baseline user input device (200) orientation matrix at a time determined by the user, for example, when a user interacts with the user input device (200) to indicate a clutch or clutching. After the clutch and baseline data capture, robotic surgical system (10) continuously captures the orientation of the user input device (200) in real-time. Data capture could be managed by a processor and memory either of the user input device (200), or another processing device (20, 30, 40) in communication with the user input device (200). The processor configured for data capture could receive a clutch signal based upon an input from the user to the user input device (200) then capture the 3-axis orientation of the user input device (200) using, for example, magnetic sensors, optical tracking devices, accelerometer and gyroscopic sensors, and/or other similar devices that may be used to determine the position and orientation of a device within three-dimensional space. Data captured could also include a baseline sample of joint angles from the surgical instrument (300).

Robotic surgical system (10) may also derive (block 1002) a rotation matrix to determine the matrix necessary to convert the baseline orientation matrix to the real time orientation matrix, which may be referred to as the Rotation Matrix. The Rotation Matrix may be determined based upon the transpose of the baseline orientation matrix pre-multiplied by the real-time orientation matrix, as shown below in Equation I.

$$(\text{Baseline Orientation Matrix})*(\text{Real-Time Orientation Matrix})^T \quad \text{Equation I:}$$

In addition to determining the Rotation Matrix, the robotic surgical system (10) may use derive (block 1004) the input axis and $\theta_{in}$ angle. In some implementations, this can be performed by using the Euler rotation theorem to find the equivalent axis and angle necessary to have the effect of the Rotation Matrix. This could be performed by, for example, finding the eigenvector of the Rotation matrix, where the Eigen value equals 1 and finding the angle by solving the following Equation II.

$$\text{Trace}(\text{Rotation Matrix})=1+2*\cos(\theta_{in}). \quad \text{Equation II:}$$

The Input Axis could be stored in the system as the scalars with sum of 1. Each scalar would pertain to the component of the Input Axis that coincides with the x, y and z axis of the global coordinate system.

Figure 7:
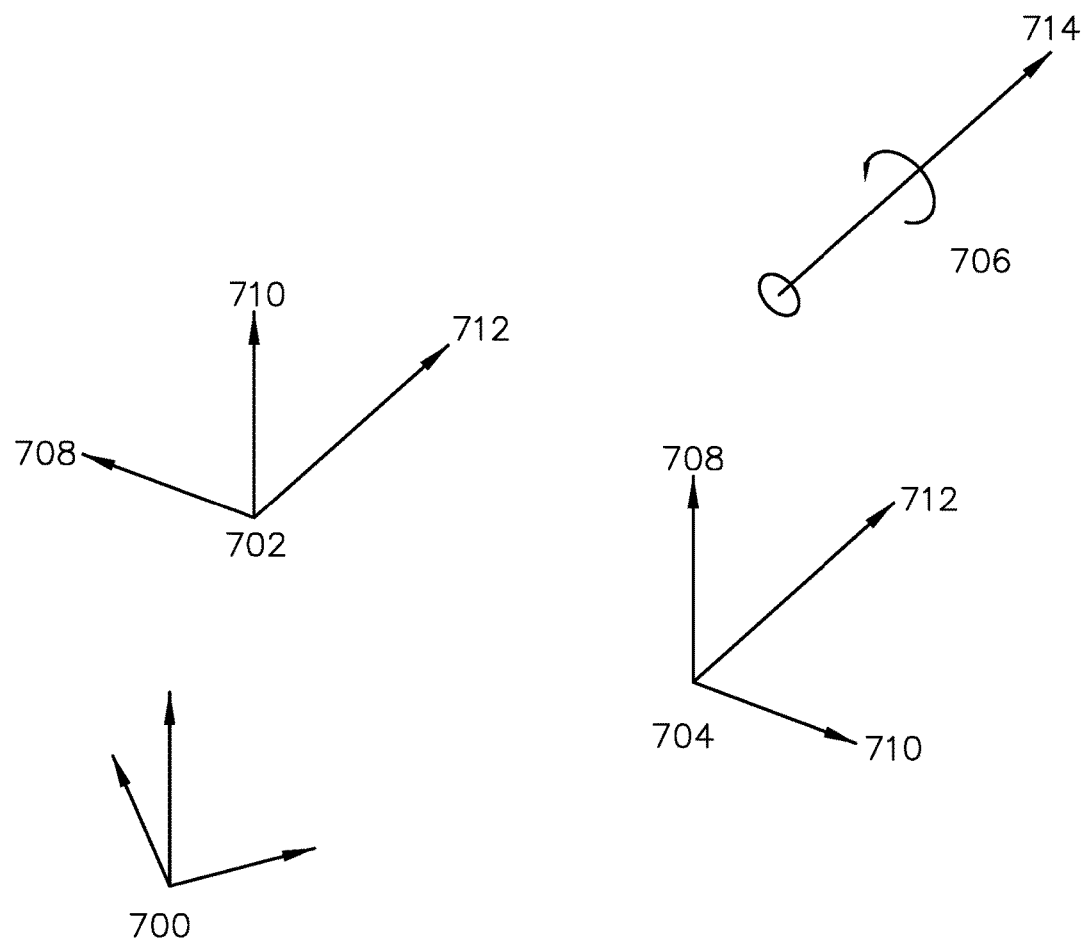
FIG. 7 depicts an exemplary diagram of rotational displacements applied to a three-dimensional coordinate system relative to a global coordinate system.

FIG. 7 shows a hypothetical rotation of a surgical instrument (not pictured) along an input axis, relative to a global coordinate system (700) as described above, FIG. 7 shows the z-axis, k-hat position (708), x-axis, i-hat position (710), and y-axis, j-hat position (712) at t=a+Δt (702). After a rotation of $\theta_{in}$ from t=a+Δt to t=a (706), FIG. 7 shows the shows the z-axis, k-hat position (708), x-axis, i-hat position (710), and y-axis, j-hat position (712) at t=a (704).

Robotic surgical system (10) may also generate (block 1006) overlaps between the Input Axis and each of the axes associated with a joint angle target. This may be determined by taking the dot product of the Input Axis and the associated joint angle target axis. For example, if the user rotates the user input device (200) along an axis parallel to the shaft (302) of the instrument (300), the overlap will be 1 or 100% for the shaft (302) joint angle target. If the user rotates the user input device (200) along an axis perpendicular to the shaft (302) of the instrument (300), the overlap will be 0 or 0% for the shaft (302) joint angle target. Rotation along axes between perpendicular and parallel may have varying values between 0% and 100%.

Figure 8:
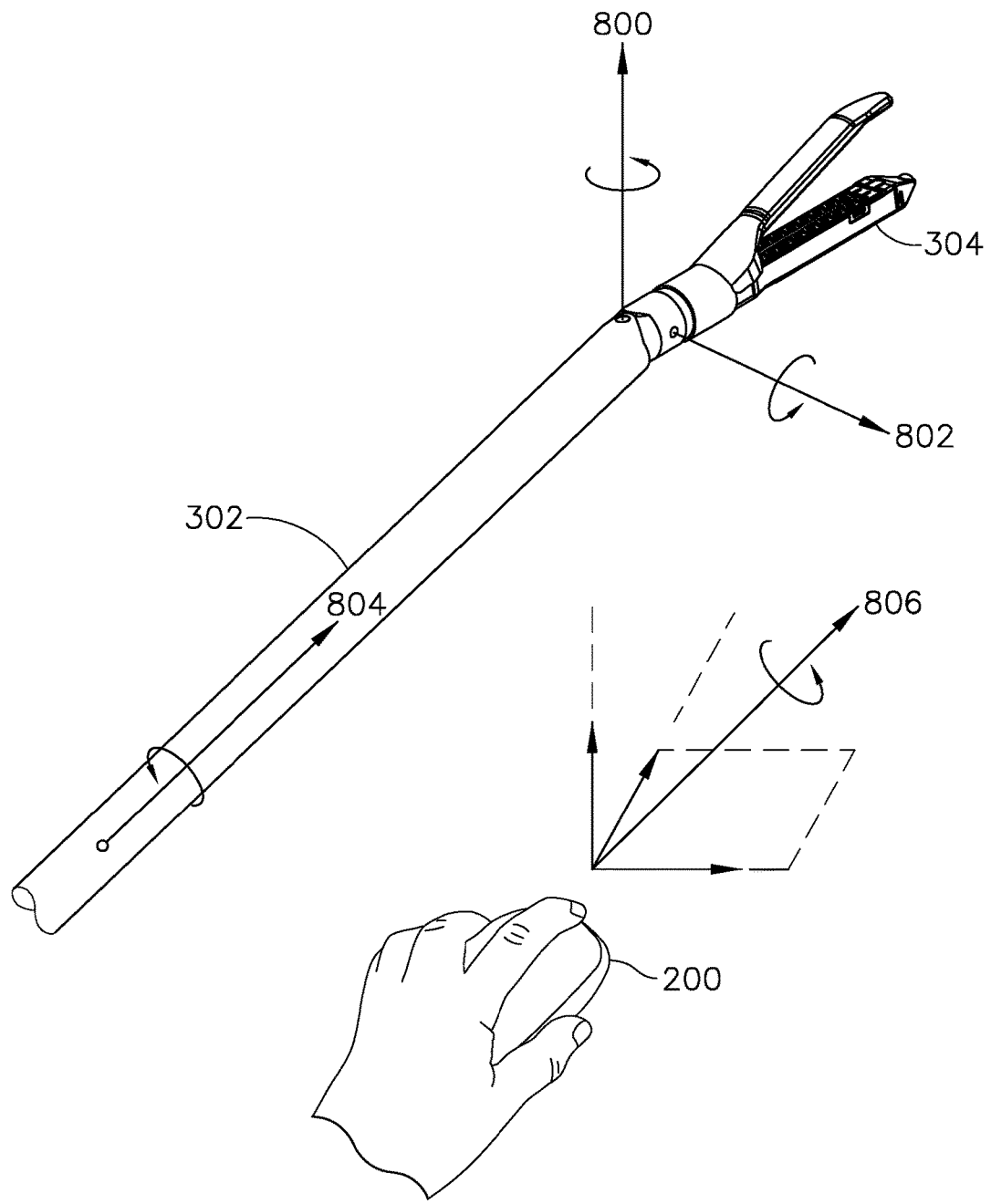
FIG. 8 depicts the movement of an end effector of a surgical instrument corresponding to the movement of the user input device of FIG. 2.

FIG. 8 shows a shaft (302) and end effector (304) of a surgical instrument (300) relative to a gripped user input device (200). The end effector (304) in this example is capable of yaw rotation about the z-axis (800), pitch rotation about the x-axis (802), and shaft rotation about the y-axis (804). In this example, the user has clutched the user input device (200) to indicate that inputs should cause movement of the end effector (304) corresponding to movement of the user input device (200) along an input axis (806).

After overlaps have been determined, robotic surgical system (10) may correct (block 1008) the overlaps to minimize the effect of input data that may result in unintentional movements. Using a threshold for input values, unintended movement may be eliminated by modifying the raw overlap previously generated (block 1006) for each joint angle target to ignore any overlap that has a magnitude of less than a configured threshold. Thresholds may be global thresholds or joint specific thresholds, depending upon a particular implementation. After ignoring overlap that falls below a threshold, the remaining overlap may be scaled to reflect any overlap that fell below the threshold.

Figure 9:
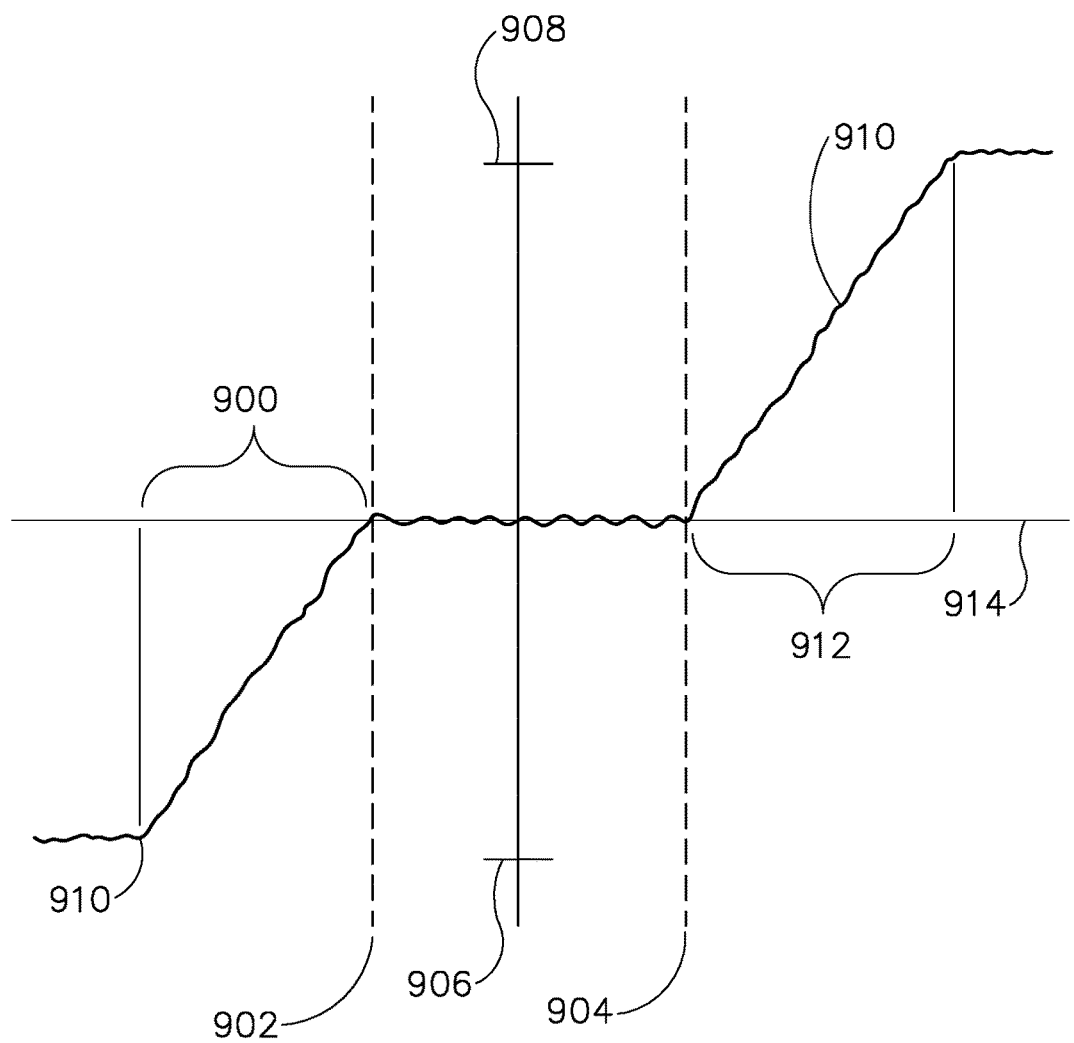
FIG. 9 depicts a graph of raw and converted overlap data generated from the user input device of FIG. 2.

FIG. 9 shows a visualization of an exemplary function that could serve as a correction method. Raw overlap (914) is applied to the horizontal axis and the output, as corrected overlap (910) is shown along the graph. Corrected overlap (910) within a threshold lower limit (902) and upper limit (904) matches raw overlap (914). Below the threshold lower limit (902), corrected overlap (910) monotonically decreases (900) below raw overlap (914), while above the threshold upper limit (904) corrected overlap (910) monotonically increases (910) above raw overlap (914). At all points in the graph, corrected overlap (910) falls between the overlap lower limit (906) and the overlap upper limit (908). The visualization of FIG. 9 shows that within a certain threshold, overlap is taken at its raw unmodified value. Below that threshold, overlap is corrected to reduce its impact on instrument motion, and above that threshold overlap is corrected to magnify its impact on instrument motion.

With corrected overlap having been determined, the system may then update (block 1010) the joint angle targets for one or more joints of the surgical instrument. Joint angle targets may be updated based upon the baseline angle for the joint target initially stored (block 1000), the input axis and angle previously stored (block 1004), and the determined corrected overlap (block 1008). An exemplary calculation that may be used to calculate a generic joint angle update is shown in Equation III below, while an exemplary calculation that may be used to determine the yaw joint angle target is shown in Equation IV below.

$$\theta_{new}=\theta_{baseline}+\theta_{input}*\text{correctedOverlap} \quad \text{Equation III:}$$

$$\theta_{yaw\text{-}new}=\theta_{yaw\text{-}baseline}+\theta_{input}*\text{correctedOverlap}_{yaw} \quad \text{Equation IV:}$$

In addition to determining updated values for joint angle targets (block 1010), robotic surgical system (10) may also determine (block 1012) limits for joint angle targets. Due to hardware constraints of a particular surgical instrument (300), the range of achievable joint angle targets may be limited. Thus, if a new joint angle target is determined that falls outside that achievable range, it must be handled appropriately to avoid damage to the instrument (300) or confusion between the user and robotic surgical system (10) that may lead to unintended movements of the surgical instrument (300). To address this, hardware joint limits may be stored in the instrument (300) itself or within robotic surgical system (10) and used to provide minimum and maximum range values for achievable joint positions. One exemplary calculation that may be used to determine a generic limited joint angle target is shown below in Equation V, while an exemplary calculation that may he used to determine a yaw joint angle target is shown below in Equation VI.

$$\theta_{final} = \max(\min(\theta_{new}, upperlimit), lowerlimit) \quad \text{Equation V:}$$

$$\theta_{yaw\text{-}final} = \max(\min(\theta_{yaw\text{-}new}, upperlimit_{yaw}), lowerlimit_{yaw}) \quad \text{Equation VI:}$$

Once modified to fall within joint angle limits (block 1012), the joint angle targets may be provided (block 1014) to the operation assembly (40) via the data transmission unit (30). Once received by the operation assembly (40), the new joint angle targets may be verified based upon joint angle limitations or other safety protocols and then used to produce movements in the surgical instrument (300) corresponding to the corrected input.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A system comprising: (a) a user input device comprising a position sensor, wherein the position sensor is configured to generate position data in response to movement and rotation of the user input device in a first number of degrees of freedom; (b) a robotic surgical system comprising a surgical instrument, wherein the robotic surgical system is configured to manipulate at least a first portion of the surgical instrument in a second number of degrees of freedom based upon receiving a joint angle target; and (c) a position data manager comprising a processor and memory, wherein the position data manager is communicatively coupled with the user input device and the robotic surgical system; wherein the first number of degrees of freedom is greater than the second number of degrees of freedom, and wherein the position data manager is configured to: (i) receive a set of position data from the user input device for the first number of degrees of freedom, the set of position data comprising a set of baseline position data and a set of real time position data, (ii) generate a set of raw overlap data based upon the set of position data, (iii) generate a set of corrected joint angle targets for the second number of degrees of freedom based upon the set of raw overlap data and an overlap threshold, and (iv) provide the set of corrected joint angle targets to the robotic surgical system.

EXAMPLE 2

The system of Example 1, wherein the position sensor comprises one or more of: (i) a magnetic field position sensor, (ii) an optical trackingposition sensor, or (iii) an accelerometer and gyroscopic position sensor.

EXAMPLE 3

The system of any one or more of Examples 1 through 2, wherein the first number of degrees of freedom comprises two or more of: (i) forward and back, (ii) up and down, (iii) left and right, (iv) yaw, (v) pitch, or (vi) roll, and wherein the second number of degrees of freedom comprises five or less of: (i) forward and back, (ii) up and down, (i) left and ht, (iv) yaw, (v) pitch, or (vi) roll.

EXAMPLE 4

The system of any one or more of Examples 1 through 3, wherein the position data manager is integral with the user input device.

EXAMPLE 5

The system of any one or more of Examples 1 through 4, wherein the position data manager is integral with the robotic surgical system.

EXAMPLE 6

The system of any one or more of Examples 1 through 5, further comprising a clutch input feature, wherein the clutch input feature is operable to place the user input device in a clutch mode, wherein the position data manager is configured to receive the position data in response to activation of the clutch input feature, and wherein position data manager is configured to collect the set of real time position data only while the user input device is in the clutch mode.

EXAMPLE 7

The system of any one or more of Examples 1 through 6, wherein the position data manager is further configured to: (i) derive a rotation matrix based upon the set of baseline position data and the set of real time position data, (ii) derive an input axis and input angle based upon the rotation matrix, and (iii) generate the set of raw overlap based upon the input axis and input angle.

EXAMPLE 8

The system of Example 7, wherein the position data manager is further configured to generate the set of corrected joint angle targets for the second number of degrees of freedom based upon the input angle, input axis, and a set of corrected overlap data.

EXAMPLE 9

The system of Example 8, wherein the position data manager is further configured to generate the set of corrected overlap data by setting to zero any value within the set of raw overlap data whose magnitude is less than the overlap threshold.

EXAMPLE 10

The system of any one or more of Examples 1 through 9, wherein the position data manager is further configured to limit the maximum and minimum values of the set of corrected joint angle targets for the second number of degrees of freedom based upon a set of range of motion limits for the surgical instrument.

EXAMPLE 11

The system of any one or more of Examples 1 through 10, wherein the user input device comprises a wireless handheld device.

EXAMPLE 12

The system of any one or more of Examples 1 through 11, wherein the surgical instrument comprises two or more portions that may be manipulated by the robotic surgical system independently of each other.

EXAMPLE 13

The system of Example 12, wherein the position sensor is configured to generate position data for each of the two or more portions of the surgical instrument simultaneously.

EXAMPLE 14

The system of Example 13, wherein the position sensor is configured to generate position data only for a selected portion of the two or more portions.

EXAMPLE 15

The system of any one or more of Examples 1 through 14, wherein the position data manager is configured to determine the overlap threshold based upon one or more of (i) the entire surgical instrument, or (ii) the first portion of the surgical instrument.

EXAMPLE 16

A system comprising: (a) a user input device comprising a position sensor, wherein the position sensor is configured to generate position data in response to movement and rotation of the user input device in a first number of degrees of freedom; (b) a clutch input operable to generate a clutching signal in response to user input indicating a ready state for the user input device; (c) a robotic surgical system comprising a surgical instrument, wherein the robotic surgical system is configured to manipulate at least a first portion of the surgical instrument in a second number of degrees of freedom based upon receiving a joint angle target; (d) a position data manager comprising a processor and memory, wherein the position data manager is communicatively coupled with the user input device and the robotic surgical system; wherein the first number of degrees of freedom is greater than the second number of degrees of freedom, and wherein the position data manager is configured to: (i) receive a clutching signal from the clutch input in response to user input indicating a ready state for the user input device, (i) in response to receiving the clutching signal, obtain a set of baseline position data and a set of real time position data from the user input device, (iii) derive a rotation matrix based upon the set of baseline position data and the set of real time position data, (iv) derive one or more of an input axis and an input angle based upon the rotation matrix, (v) determine a set of raw overlap data based upon one or more of the input axis and the instrument axes, (vi) determine a set of corrected overlap data by setting to zero any value in the set of raw overlap data whose magnitude is less than an overlap threshold, (vii) determine a set of joint angle targets based upon the set of baseline position data and the set of corrected overlap data, and (viii) provide the set of joint angle targets to the robotic surgical system.

EXAMPLE 17

The system of Example 16, wherein the clutch input is integral with the user input device.

EXAMPLE 18

The system of any one or more of Examples 16 through 17, wherein the position data manager is further configured to limit the maximum and minimum values of the set of joint angle targets based upon a set of range of motion limits for the surgical instrument.

EXAMPLE 19

The system of any one or more of Examples 16 through 18, wherein the surgical instrument comprises two or more portions that may be manipulated by the robotic surgical system independently of each other, and wherein the user input device is configured to selectively: (i) generate baseline position data for each of the two or more portions simultaneously, or (ii) generate baseline position data for only one of the two or more portions.

EXAMPLE 20

A method comprising the steps: (a) receiving at a position data manager a set of position data from a position sensor of one or more instrument axes associated with an input device, the set of position data comprising a set of baseline position data and a set of real time position data within a first number of degrees of freedom; (b) generating a set of raw overlap data based upon the set of position data and instrument axes; (c) generating a set of corrected joint angle targets for a second number of degrees of freedom based upon the set of raw overlap data and an overlap threshold; and (d) providing the set of corrected joint angle targets to a surgical instrument of a robotic surgical system, wherein the surgical instrument is adapted to move within the second number of degrees of freedom based upon the set of corrected joint angle targets being received by the robotic surgical system, and wherein the first number of degrees of freedom is greater than the second number of degrees of freedom.

IV. Miscellaneous

To the extent that the terms "position" and "orientation" are used separately herein, it should be understood that, unless otherwise explicitly noted, the term "position" may include rotational positioning (i.e., angular orientation) of an object within a three-dimensional space in addition to including the linear location of an object within a three-dimensional space. In other words, the term "position"

should not be read as necessarily excluding angular orientation since angular orientation may be regarded as rotational positioning.

It should also be understood that the teachings herein may be readily combined with the teachings of U.S. Pub. No. 2017/0095298, entitled "User Input Device for Robotic Surgical System," published Apr. 6, 2017, the disclosure of which is incorporated by reference herein. Various suitable ways in which the teachings herein may be combined with the teachings of U.S. Pub. No. 2017/0095298, published Apr. 6, 2017 will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geomettics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A system comprising:
   (a) a user input device comprising a position sensor, wherein the position sensor is configured to generate position data in response to movement and rotation of the user input device in a first number of degrees of freedom;
   (b) a robotic surgical system comprising a surgical instrument, wherein the robotic surgical system is configured to manipulate at least a first portion of the surgical instrument in a second number of degrees of freedom based upon receiving a joint angle target; and
   (c) a position data manager comprising a processor and memory, wherein the position data manager is communicatively coupled with the user input device and the robotic surgical system;
   wherein the first number of degrees of freedom is greater than the second number of degrees of freedom, and wherein the position data manager is configured to:
      (i) receive a set of position data from the user input device for the first number of degrees of freedom, the set of position data comprising a set of baseline position data and a set of real time position data,
      (ii) generate a set of raw overlap data based upon the set of position data,
      (iii) generate a set of corrected joint angle targets for the second number of degrees of freedom based upon the set of raw overlap data and an overlap threshold, and (iv) provide the net of corrected joint angle targets to the robotic surgical system.

2. The system of claim 1, wherein the position sensor comprises one or more of:
(i) a magnetic field position sensor,
(ii) an optical tracking position sensor, or
(iii) an accelerometer and gyroscopic position sensor.

3. The system of claim 1, wherein the first number of degrees of freedom comprises two or more of:
(i) forward and back,
(ii) up and down,
(iii) left and right,
(iv) yaw,
(v) pitch, or
(vi) roll, and
wherein the second number of degrees of freedom comprises five or less of:
(i) forward and back,
(ii) up and down,
(iii) left and right,
(iv) yaw,
(v) pitch, or
(vi) roll.

4. The system of claim 1, wherein the position data manager is integral with the user input device.

5. The system of claim 1, wherein the position data manager is integral with the robotic surgical system.

6. The system of claim 1, further comprising a clutch input feature, wherein the clutch input feature is operable to place the user input device in a clutch mode, wherein the position data manager is configured to receive the position data in response to activation of the clutch input feature, and wherein position data manager is configured to collect the set of real time position data only while the user input device is in the clutch mode.

7. The system of claim 1, wherein the position data manager is further configured to:
(i) derive a rotation matrix based upon the set of baseline position data and the set of real time position data,
(ii) derive an input axis and input angle based upon the rotation matrix, and
(iii) generate the set of raw overlap based upon the input axis and input angle.

8. The system of claim 7, wherein the position data manager is further configured to generate the set of corrected joint angle targets for the second number of degrees of freedom based upon the input angle, input axis, and a set of corrected overlap data.

9. The system of claim 8, wherein the position data manager is further configured to generate the set of corrected overlap data by setting to zero any value within the set of raw overlap data whose magnitude is less than the overlap threshold.

10. The system of claim 1, wherein the position data manager is further configured to limit the maximum and minimum values of the set of corrected joint angle targets for the second number of degrees of freedom based upon a set of range of motion limits for the surgical instrument.

11. The system of claim 1, wherein the user input device comprises a wireless handheld device.

12. The system of claim 1, wherein the surgical instrument comprises two or more portions that may be manipulated by the robotic surgical system independently of each other.

13. The system of claim 12, wherein the position sensor is configured to generate position data for each of the two or more portions of the surgical instrument simultaneously.

14. The system of claim 13, wherein the position sensor is configured to generate position data only for a selected portion of the two or more portions.

15. The system of claim 1, wherein the position data manager is configured to determine the overlap threshold based upon one or more of:
(i) the entire surgical instrument, or
(ii) the first portion of the surgical instrument.

16. A system comprising:
(a) a user input device comprising a position sensor, wherein the position sensor is configured to generate position data in response to movement and rotation of the user input device in a first number of degrees of freedom;
(b) a clutch input operable to generate a clutching signal in response to user input indicating a ready state for the user input device;
(c) a robotic surgical system comprising a surgical instrument, wherein the robotic surgical system is configured to manipulate at least a first portion of the surgical instrument in a second number of degrees of freedom based upon receiving a joint angle target;
(d) a position data manager comprising a processor and memory, wherein the position data manager is communicatively coupled with the user input device and the robotic surgical system;
wherein the first number of degrees of freedom is greater than the second number of degrees of freedom, and wherein the position data manager is configured to:
(i) receive a clutching signal from the clutch input in response to user input indicating a ready state for the user input device,
(ii) in response to receiving the clutching signal, obtain a set of baseline position data and a set of real time position data from the user input device,
(iii) derive a rotation matrix based upon the set of baseline position data and the set of real time position data,
(iv) derive one or more of an input axis and an input angle based upon the rotation matrix,
(v) determine a set of raw overlap data based upon one or more of the input axis and the instrument axes,
(vi) determine a set of corrected overlap data by setting to zero any value in the set of raw overlap data whose magnitude is less than an overlap threshold,
(vii) determine a set of joint angle targets based upon the set of baseline position data and the set of corrected overlap data, and
(viii) provide the set of joint angle targets to the robotic surgical system.

17. The system of claim 16, wherein the clutch input is integral with the user input device.

18. The system of claim 16, wherein the position data manager is further configured to limit the maximum and minimum values of the set of joint angle targets based upon a set of range of motion limits for the surgical instrument.

19. The system of claim 16, wherein the surgical instrument comprises two or more portions that may be manipulated by the robotic surgical system independently of each other, and wherein the user input device is configured to selectively:
(i) generate baseline position data for each of the two or more portions simultaneously, or
(ii) generate baseline position data for only one of the two or more portions.

20. A method comprising the steps:
(a) receiving at a position data manager a set of position data from a position sensor of one or more instrument axes associated with an input device, the set of position data comprising a set of baseline position data and a set of real time position data within a first number of degrees of freedom;
(b) generating a set of raw overlap data based upon the set of position data and instrument axes;
(c) generating a set of corrected joint angle targets for a second number of degrees of freedom based upon the set of raw overlap data and an overlap threshold; and
(d) providing the set of corrected joint angle targets to a surgical instrument of a robotic surgical system,
wherein the surgical instrument is adapted to move within the second number of degrees of freedom based upon the set of corrected joint angle targets being received by the robotic surgical system, and wherein the first number of degrees of freedom is greater than the second number of degrees of freedom.

* * * * *